(12) United States Patent
Goredema et al.

(10) Patent No.: US 8,952,191 B2
(45) Date of Patent: *Feb. 10, 2015

(54) ESTER RESIN COMPOSITIONS

(71) Applicant: Xerox Corporation, Norwalk, CT (US)

(72) Inventors: Adela Goredema, Mississauga (CA); Rina Carlini, Oakville (CA); Jennifer L. Belelie, Oakville (CA); Naveen Chopra, Oakville (CA); Kentaro Morimitsu, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 9 days.

This patent is subject to a terminal disclaimer.

(21) Appl. No.: 13/680,200

(22) Filed: Nov. 19, 2012

(65) Prior Publication Data

US 2014/0142335 A1 May 22, 2014

(51) Int. Cl.
C07C 69/74 (2006.01)
C07C 69/70 (2006.01)
C07C 69/40 (2006.01)
C07C 69/533 (2006.01)
C07C 69/675 (2006.01)

(52) U.S. Cl.
CPC ............. C07C 69/70 (2013.01); C07C 69/40 (2013.01); C07C 69/533 (2013.01); C07C 69/675 (2013.01)
USPC ................................................. 560/117

(58) Field of Classification Search
None
See application file for complete search history.

(56) References Cited

U.S. PATENT DOCUMENTS

| | | | |
|---|---|---|---|
| 5,195,430 A | 3/1993 | Rise | |
| 5,231,135 A | 7/1993 | Machell et al. | |
| 5,372,852 A | 12/1994 | Titterington et al. | |
| 5,389,958 A | 2/1995 | Bui et al. | |
| 5,496,879 A | 3/1996 | Griebel et al. | |
| 5,621,022 A | 4/1997 | Jaeger et al. | |
| 5,750,604 A * | 5/1998 | Banning et al. | ............... 524/187 |
| 6,221,137 B1 | 4/2001 | King et al. | |
| 6,472,523 B1 | 10/2002 | Banning et al. | |
| 6,547,380 B2 | 4/2003 | Smith et al. | |
| 6,590,082 B1 | 7/2003 | Banning et al. | |
| 6,646,111 B1 | 11/2003 | Carlini et al. | |
| 6,713,614 B2 | 3/2004 | Carlini et al. | |
| 6,958,406 B2 | 10/2005 | Banning et al. | |
| 6,998,493 B2 | 2/2006 | Banning et al. | |
| 7,063,410 B2 | 6/2006 | Slotto et al. | |
| 7,211,131 B2 | 5/2007 | Banning et al. | |
| 7,294,730 B2 | 11/2007 | Banning et al. | |
| 7,381,831 B1 | 6/2008 | Banning et al. | |
| 7,427,323 B1 | 9/2008 | Birau et al. | |
| 7,448,719 B1 | 11/2008 | Newell | |

(Continued)

FOREIGN PATENT DOCUMENTS

GB 1257940 * 12/1971

OTHER PUBLICATIONS

Database Caplus Chemical Abstracts Service, Columbus, Ohio, US; Database Accession No. 1966:491497, Abstract of FR 1429486 ESSO Research and Engineering Co. Feb. 25, 1966.*

(Continued)

Primary Examiner — Karl J Puttlitz
(74) Attorney, Agent, or Firm — Pillsbury Winthrop Shaw Pittman LLP

(57) ABSTRACT

A composition including one or more ester resins useful for various applications is disclosed. For example, the composition including one or more ester resins may function as a component that is incorporated into an ink composition.

20 Claims, 1 Drawing Sheet

(56) References Cited

U.S. PATENT DOCUMENTS

| | | | |
|---|---|---|---|
| 7,465,348 | B1 | 12/2008 | Carlini et al. |
| 7,503,973 | B1 | 3/2009 | Carlini |
| 7,732,581 | B2 | 6/2010 | Banning et al. |
| 7,905,954 | B2 | 3/2011 | Carlini et al. |
| 2010/0086683 | A1 | 4/2010 | Birau et al. |

OTHER PUBLICATIONS

Database Caplus Chemical Abstracts Service, Columbus, Ohio, US; Database Accession No. 1972:100686, Abstract of GB 1257940, Citrone et al., British Oxygen Co. Ltd. Dec. 22, 1971.*

Database Caplus Chemical Abstracts Service, Columbus, Ohio, US; Database Accession No. 1998:116128, Abstract of US 5750604 and family.*

U.S. Appl. No. 13/095,636, filed Apr. 27, 2011, to Belelie et al.
U.S. Appl. No. 13/680,322, filed Nov. 19, 2012, to Goredema et al.
U.S. Appl. No. 13/681,106, filed Nov. 19, 2012, to Goredema et al.
U.S. Appl. No. 13/680,818, filed Nov. 19, 2012, to Goredema et al.
U.S. Appl. No. 13/681,206, filed Nov. 19, 2012, to Vanbesien et al.
U.S. Appl. No. 13/680,237, filed Nov. 19, 2012, to Carlini et al.
U.S. Appl. No. 13/680,271, filed Nov. 19, 2012, to Carlini et al.

\* cited by examiner

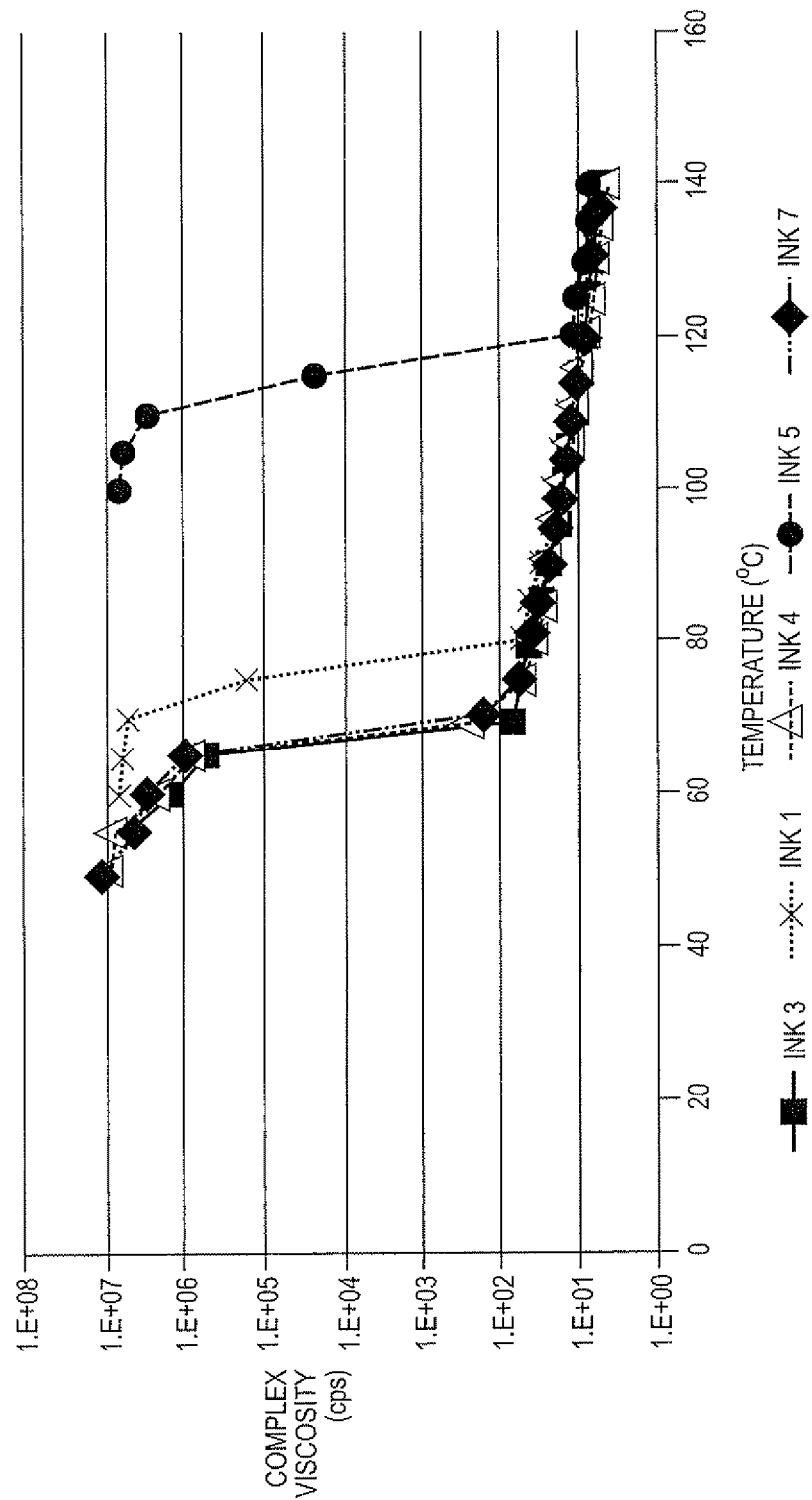

ESTER RESIN COMPOSITIONS

CROSS-REFERENCE TO RELATED APPLICATIONS

Commonly assigned U.S. patent application Ser. No. 13/680,322, (entitled "Ink Compositions Incorporating Ester Resins") to Adela Goredema et al.; commonly assigned U.S. patent application Ser. No. 13/681,206, (entitled "Bio-Renewable Phase Change Inks Comprising Recycled Resin Materials") to Daryl W. Vanbesien et al.; commonly assigned U.S. patent application Ser. No. 13/681,106, (entitled "Bio-renewable Fast Crystallizing Phase Change Inks) to Adela Goredema et al.; commonly assigned U.S. patent application Ser. No. 13/680,237, (entitled "Oligomeric Rosin Esters for Use in Inks") to Rina Carlini et al.; commonly assigned U.S. patent application Ser. No. 13/680,271, (entitled "Phase Change Inks Containing Oligomeric Rosin Esters") to Rina Carlini et al.; commonly assigned U.S. patent application Ser. No. 13/095,636, entitled Solid Ink Compositions Comprising Crystalline-Amorphous Mixtures" to Jennifer Belelie et al.; and commonly assigned U.S. patent application Ser. No. 13/196,157, entitled "Phase Change Inks Containing Crystalline Polyterpene resins" to Rina Carlini et al., the entire disclosures of which are totally incorporated herein by reference in their entireties.

TECHNICAL FIELD

This disclosure is generally directed to compositions comprising ester resins or compounds, such as Abitol E ester resins or compounds. Such compositions may be incorporated into various other substances, such as ink compositions and/or as components for ink compositions, such as binder agents and/or resins,

BACKGROUND

Phase change inks (sometimes referred to as "solid inks" and "hot melt inks") have been used in various liquid deposition techniques. Phase change inks often contain a "phase-change agent" that enables the ink to exist in a solid phase at ambient temperatures, but also exist in the liquid phase at the elevated operating temperature of an ink jet printing device. At the deposit operating temperature, droplets of liquid ink are ejected from the printing device and, as the ink is jetted towards or contacts the surface of the recording substrate, either directly or via an intermediate heated transfer belt or drum, the ink rapidly solidifies onto the substrate to form a predetermined pattern of solidified ink marks. Phase change inks have also been used in other printing technologies, such as gravure printing, as disclosed in, for example, U.S. Pat. No. 5,496,879, the entire disclosure of which is totally incorporated herein by reference. Phase change inks have also been used for applications such as postal marking, industrial marking, and labeling.

Phase change inks are desirable for ink jet printers because they remain in a solid phase at room temperature, which is convenient during shipping and ink handling, enables long term storage, and ease of use. In addition, the problems associated with nozzle clogging as a result of ink evaporation with liquid ink jet inks are largely eliminated, thereby greatly improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and image quality is improved.

Ink jet printing systems generally are of two types: continuous stream and drop-on-demand, as described in U.S. Pat. No. 6,547,380. The entire disclosures of U.S. Pat. Nos. 5,195,430 and 6,547,380 are totally incorporated herein by reference.

There are at least three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. Still another type of drop-on-demand system is known as thermal ink jet, or bubble jet, and produces high velocity droplets.

In a typical design of a piezoelectric ink jet device utilizing phase change inks printing directly on a substrate or on an intermediate transfer member, such as the ones described in U.S. Pat. Nos. 5,372,852; 7,063,410; and 7,448,719 the disclosures of which are hereby incorporated by reference in their entireties. At the jet operating temperature, droplets of liquid ink are ejected from the printing device and, when the ink droplets contact the surface of the recording substrate, either directly or via an intermediate heated transfer belt or drum, they rapidly solidify to form a predetermined pattern of solidified ink drops. This approach simplifies the printhead design, and the small movements ensure good droplet registration and allows for printing directly on a substrate or on an intermediate transfer member.

Phase change inks for use in such jet printing systems generally are in the solid phase at, for example, ambient or room temperature, such as about 20° C. to about 25° C., but exist in the liquid phase at the elevated operating temperature of an ink jet printing device. At the jet operating temperature, the ink is molten and droplets of liquid ink are ejected from the printing device. In order to display such properties, known phase change inks generally contain components such as crystalline waxes and other materials that enable sharp and rapid phase transitions from the molten liquid state to the solid state. Many known phase change inks, however, exhibit disadvantages such as poor adhesion to coated paper substrates, resulting in poor scratch-resistance, poor image robustness, hard and brittle properties, poor 'paper fold' performance such as cracking and creasing of the image when the document is folded, and document offset. Further, the nonpolarity of these ink components often leads to compatibility issues with commonly available dyes and pigments, resulting in the need for more expensive or custom-designed colorants to ensure good solubility or dispersibility in the ink carrier and good long-term thermal stability to prevent colorant degradation or colorant migration.

Customers have also created a demand for materials that are bio-renewable or derived at least partly from renewable resources. Energy and environmental policies, increasing and volatile oil prices, and public/political awareness of the rapid depletion of global fossil reserves have created a need to find sustainable monomers derived from bio-renewable materials. By using biorenewable feedstock, manufacturers can reduce their carbon footprint and move to a zero-carbon or even a carbon-neutral footprint.

Accordingly, while known materials and processes are suitable for their intended purposes, there is a need for improved phase change inks. In addition, there is a need for phase change inks that exhibit sharp and rapid phase transitions from the molten liquid state to the solid state. Further, there is a need for phase change inks that exhibit good adhesion to coated paper substrates. Additionally, there is a need for phase change inks that exhibit good scratch-resistance. There is also a need for phase change inks that exhibit good image robustness. In addition, there is a need for phase change inks that exhibit good "paper fold" performance and reduced cracking and creasing of the image when the document is folded. Further, there is a need for phase change inks that exhibit good document offset performance. Additionally, there is a need for phase change inks that exhibit good compatibility with commonly available colorants. In addition, a need remains for phase change inks that contain at least some materials at least partly derived from renewable resources. Further, a need remains for phase change inks that can be prepared at desirably low cost. There is also a need for phase change inks that contain some biodegradable components. These and other needs and advantages can be achievable with the compositions comprising ester resins, such as Abitol ester resins of the present disclosure.

SUMMARY

Some embodiments relate to an ester composition including at least one ester compound represented by General Formula I

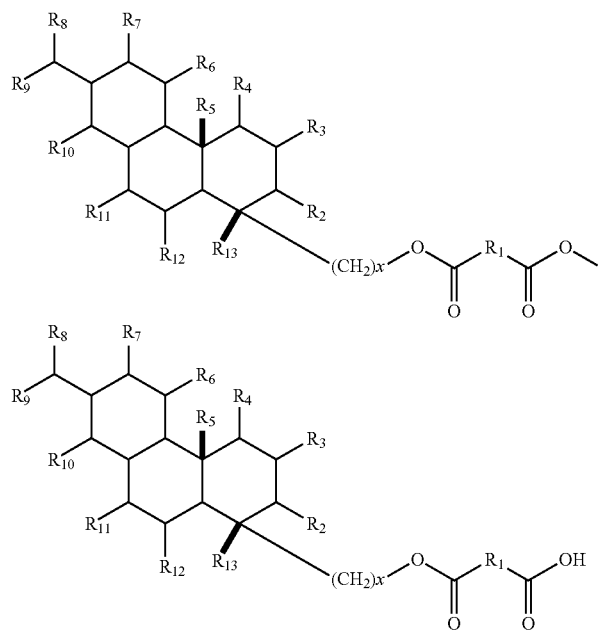
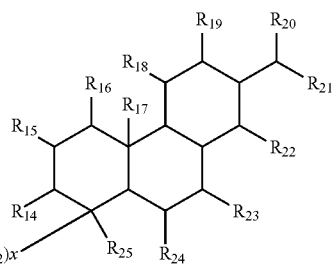
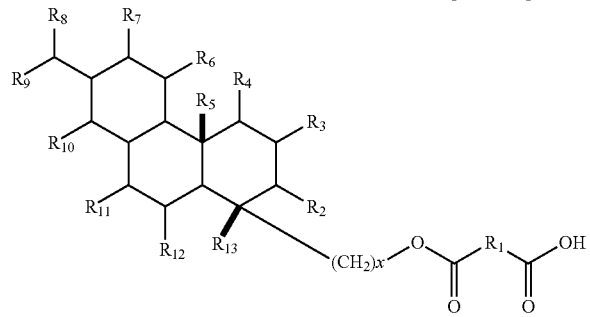

or a mixture of one or more compounds of General Formulas I and/or II;

where $R_1$ is:
(a) an alkylene group, including substituted and unsubstituted alkylene groups, wherein hetero atoms either may or may not be present in the alkylene group;
(b) an arylene group, including substituted and unsubstituted arylene groups, wherein hetero atoms either may or may not be present in the arylene group;
(c) an arylalkylene group, including substituted and unsubstituted arylalkylene groups, wherein hetero atoms either may or may not be present in either or both of the alkyl portion and the aryl portion of the arylalkylene group; or
(d) an alkylarylene group, including substituted and unsubstituted alkylarylene groups, wherein hetero atoms either may or may not be present in either or both of the alkyl portion and the aryl portion of the alkylarylene group;

two or more substituents can be joined together to form a ring; and each of $R_2$-$R_{25}$ are independently selected from the group consisting of hydrogen, alkyl groups, arylalkyl groups, alkylaryl groups, and heterocyclic groups; and wherein $(CH_2)x$ denotes one or more methylene groups.

BRIEF DESCRIPTION OF THE DRAWINGS

FIG. 1 is a graph illustrating rheology data of phase change ink samples made according to the present embodiments. All of the rheology measurements were made on a RFS3 Rheometer (TA instruments), using a 25 mm parallel plate, at a frequency of 1 Hz. The method used was a temperature sweep from high to low temperatures, in temperature steps of 5° C., a soak (equilibration) time of 120 seconds between each temperature and at a constant frequency of 1 Hz).

DESCRIPTION OF THE EMBODIMENTS

Described herein are compositions that comprise ester resins or compounds, such as Abitol E ester resins or compounds. In embodiments, such compositions may be employed, for example, as components for ink compositions, such as binder agents and/or resins.

The ester resins, such as Abitol E ester resins of this disclosure include various mono-Abitol E esters and dimer-Abitol E esters that are tethered with a spacer group. Depending on the identity of the substituent groups on the ester resins or compounds, the compounds of the present disclosure have the ability to demonstrate a variety of physical properties desirable for binder resins in that the rheological properties may be tuned. This ability to tune the rheological characteristics of some of the ester resins or compounds of this disclosure by the suitable choice of the functional group is advantageous for use in certain applications, such as for inkjet printing of phase change ink compositions.

In this specification and the claims that follow, singular forms such as "a," "an," and "the" include plural forms unless the content clearly dictates otherwise. In addition, reference may be made to a number of terms that shall be defined as follows:

The terms "one or more" and "at least one" refer, for example, to instances in which one of the subsequently described circumstances occurs, and to instances in which more than one of the subsequently described circumstances occurs.

The term "saturated" refers, for example, to compounds containing only single bonds, and in this specification, also includes cyclic structures. The term "unsaturated" refers, for example, to compounds that contain one or more double bonds and/or one or more triple bonds, which may include carbon atoms and/or heteroatoms such as O, N, S, and P.

The terms "hydrocarbon" and "alkane" refer, for example, to branched and unbranched molecules having the general formula $C_nH_{2n+2}$, in which n is an integer having a value of 1 or more, such as from 1 to about 60. Exemplary alkanes include methane, ethane, n-propane, isopropane, n-butane, isobutane, tert-butane, octane, decane, tetradecane, hexadecane, eicosane, tetracosane, isomeric forms thereof, and the like. Alkanes may be substituted by replacing hydrogen atoms with one or more functional groups. The term "aliphatic" refers, for example, to hydrocarbon molecules that are acyclic, linear or branched alkanes. The term "long-chain" refers, for example, to linear hydrocarbon chains in which n is a number of from about 8 to about 60, such as from about 18 to about 45 or from about 24 to about 40. The term "short-chain" refers, for example, to linear hydrocarbon chains in which n is a number of from 1 to about 7, such as from about 2 to about 5 or from about 3 to about 4. The term "cyclic" or "cycloaliphatic" refers, for example, to cyclic hydrocarbon molecules that comprised one or more rings, and wherein the rings can be fused, branched or polycyclic, such as a bicyclic rings.

The term "alkyl" refers, for example, to a saturated hydrocarbon group that is acyclic or cyclic, and either branched or unbranched, derived from an alkane and having the general formula $C_nH_{2n-1}$ or $C_nH_{2n-1}$, in which n is an integer having a value of 1 or more. For example, n may be in the range from 1 to about 60. Exemplary alkyl groups include methyl, ethyl, n-propyl, isopropyl, n-butyl, isobutyl, sec-butyl, tert-butyl, n-pentyl, neo-pentyl, cyclopentyl, n-hexyl, cyclohexyl, n-octyl, iso-octyl, cyclooctyl, decyl, tetradecyl, hexadecyl, eicosyl, tetracosyl, isomeric forms thereof, and the like. The term "lower alkyl" refers, for example, to an alkyl group of from 1 to about 12 carbon atoms.

The term "alkene" refers, for example, to branched and unbranched unsaturated molecules that are derived from alkenes and include one or more double bonds between carbon atoms. Exemplary alkenes include ethylene, propene, butene, butadiene, octene, decene, tetradecene, hexadecene, eicosene, tetracosene and the like. Alkenes may be substituted by replacing hydrogen atoms with one or more functional groups.

The term "aryl" refers, for example, to an organic group derived from an aromatic compound and having the same general structure as the aromatic compound. Examples of aromatic compounds include, for example, phenyl ($C_6H_5$), benzyl ($C_7H_7$), naphthyl ($C_{10}H_7$), anthracenyl ($C_{14}H_9$), furanyl ($C_4H_3O$), pyridinyl ($C_5H_4N$), thiopheneyl ($C_4H_3S$), and the like. Optionally, these aromatic groups may be substituted with one or more independently selected substituents, including alkyl and cycloalkyl, alkenyl, alkoxy, aryl, hydroxyl, thiol, halo (such as F, Cl, Br, I), (thio)ester, carboxylic acid, acyl, (alkyl)amino, (aryl)amino, and nitro groups.

The term "arylamine" refers, for example, to moieties containing both aryl and amine groups.

"Alcohol" refers, for example, to an alkyl moiety in which one or more of the hydrogen atoms has been replaced by an —OH group. The term "lower alcohol" refers, for example, to an alkyl group of about 1 to about 6 carbon atoms in which one or more of the hydrogen atoms has been replaced by an —OH group. The term "primary alcohol" refers, for example to alcohols in which the —OH group is bonded to a terminal carbon atom, such as in methanol, ethanol, 1-propanol, 1-butanol, 1-hexanol and the like. The term "secondary alcohol" refers, for example to alcohols in which the —OH group is bonded to a carbon atom that is bonded to two other carbon atoms, such as in 2-propanol (isopropanol), 2-butanol, 2-hexanol and the like. The term "tertiary alcohol" refers, for example to alcohols in which the —OH group is bonded to a carbon atom that is bonded to three other carbon atoms, such as in methylpropanol (tert-butanol) and the like.

The terms "halogen" or "halogen atom" refer, for example, to Group 7 elements such as fluorine (F), chlorine (Cl), bromine (Br), and iodine (I). The term "halo" refers, for example, to substitution of a halogen atom for a hydrogen atom in an organic compound. "Haloalkyl" refers, for example, to an alkyl moiety in which one or more of the hydrogen atoms has been replaced by a halogen atom. The term "perhalogenated" refers, for example, to a compound in which all of the hydrogen atoms have been replaced by halogen atoms, while the phrase "partially halogenated" refers, for example, to a compound in which less than all of the hydrogen atoms have been replaced by halogen atoms.

The term "alkylaryl" refers, for example, to groups comprising alkyl moiety and an aryl moiety, wherein the alkyl portion of the alkylaryl group can be linear or branched, saturated or unsaturated, and cyclic or acyclic, and wherein heteroatoms either may or may not be present in either the aryl or the alkyl portion of the alkylaryl group, with from, for example, about 6 to about 50 carbon atoms in the alkylaryl chain, such as from about 6 to about 40 or from about 7 to about 20 carbon atoms, wherein the substituents on the substituted alkyl, aryl, arylalkyl, and alkylaryl groups may be, for example, halogen atoms, ether groups, aldehyde groups, ketone groups, ester groups, amide groups, imide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring.

The term "alkylene" refers, for example, to a divalent aliphatic group or alkyl group, including linear and branched, saturated and unsaturated, cyclic and acyclic, and substituted and unsubstituted alkylene groups, and wherein heteroatoms, such as oxygen, nitrogen, sulfur, silicon, phosphorus, boron, Mg, Li, Al, Ge, Cu, Fe, Ni, Pd, Pt and the like either may or may not be present in the alkylene group. For example, an alkylene group may have the structure —$(CH_2)_p$—, in which p is an integer in a range of from 1 to about 60, such as from about 5 to about 25, or about 7 to about 15.

The term "arylene" refers, for example, to a divalent aromatic group or aryl group, including substituted and unsubstituted arylene groups, and wherein heteroatoms, such as O, N, S, P, Si, B, Al, Li, Mg, Cu, Fe and the like either may or may not be present in the arylene group. For example, an arylene group may have about 5 to about 20 carbon atoms in the arylene chain, such as from about 6 to about 14 or from about 6 to about 10 carbon atoms.

The term "arylalkylene" refers, for example, to a divalent arylalkyl group, including substituted and unsubstituted arylalkylene groups, wherein the alkyl portion of the arylalkylene group can be linear or branched, saturated or unsaturated, and cyclic or acyclic, and wherein heteroatoms, such as O, N, S, P, Si, B, Al, Li, Mg, Cu, Fe, and the like either may or may not be present in either the aryl or the alkyl portion of the arylalkylene group. For example, an arylalkylene group may have about 6 to about 32 carbon atoms in the arylalkylene chain, such as from about 7 to about 22 or from about 7 to about 20 carbon atoms.

The term "alkylarylene" refers, for example, to a divalent alkylaryl group, including substituted and unsubstituted alkylarylene groups, wherein the alkyl portion of the alkylarylene group can be linear or branched, saturated or unsaturated, and cyclic or acyclic, and wherein heteroatoms, such as O, N, S, P, Si, Ge, B, Al, Li, Mg, Cu, Fe, Pd, Pt and the like either may or may not be present in either the aryl or the alkyl portion of the alkylarylene group. For example, the alkylarylene may have about 6 to about 32 carbon atoms in the alkylarylene chain, such as from about 7 to about 22 or from about 7 to about 20 carbon atoms, wherein the substituents on the substituted alkylene, arylene, arylalkylene, and alkylarylene groups can be, for example, halogen atoms, ether groups, aldehyde groups, ketone groups, ester groups, amide groups, imide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanate groups, thiocyanato groups, isothiocyanato groups, cyano groups, pyridine groups, pyridinium groups, guanidinium groups, amidine groups, imidazolium groups, carboxylate groups, carboxylic acid groups, urethane groups, urea groups, mixtures thereof, and the like, wherein two or more substituents can be joined together to form a ring.

As used herein, the twit "viscosity" refers to a complex viscosity, which is frequency-dependent viscosity function determined during forced harmonic oscillation of shear stress. This is the typical measurement provided by a rheometer that is capable of subjecting a sample to a steady shear strain.

Ester Resins, or Compounds

In embodiments, the compositions of the present disclosure may comprise one or more ester resins or compounds, such as an ester resin or compound prepared from a diacid and an alcohol where the product of the reaction of the diacid and alcohol is biodegradable. In embodiments, the diacid and/or alcohol may be selected to be derived from a renewable resource. In specific embodiments, one or more ester resins or compounds may be Abitol E ester resins or compounds represented by a compound of General Formula I and/or General Formula II having the general structures:

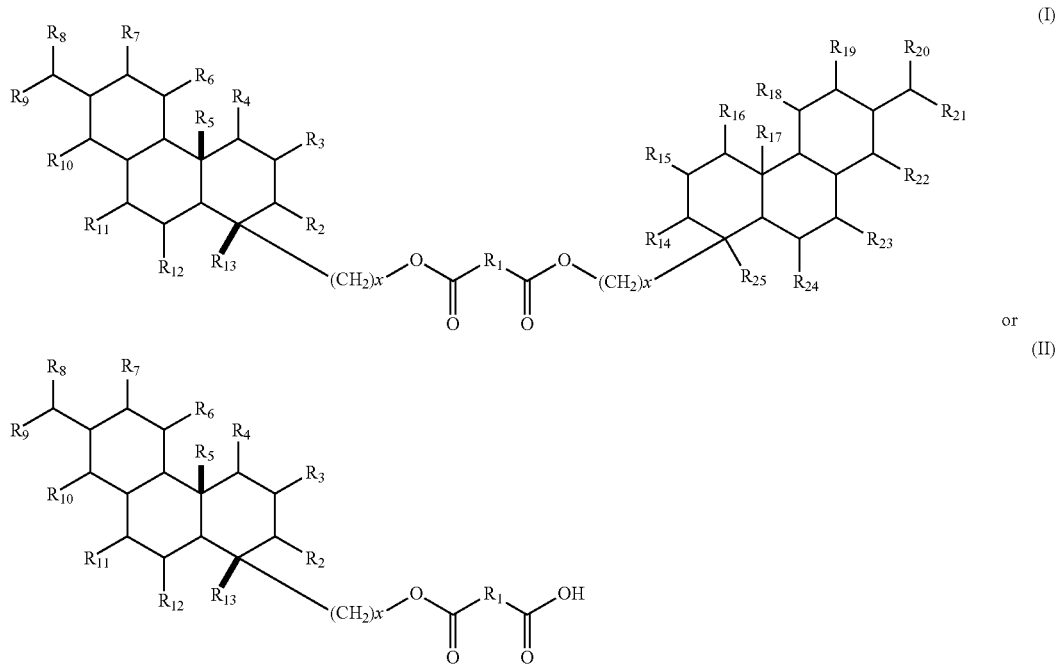

or a mixture of one or more compounds of General Formulas I and/or II;

where $R_1$ is an alkylene group, arylene group, arylalkylene group, alkylarylene group, including substituted and unsubstituted alkylene groups, and wherein hetero atoms either may or may not be present in the alkylene group such an alkylene group containing from 2 to about 60 carbon atoms, or from about 2 to about 40 carbon atoms, or from about 4 to about 10 carbon atoms, or an arylene group, arylalkylene group, alkylarylene group, including substituted and unsubstituted arylene group, arylalkylene group, alkylarylene groups, and wherein hetero atoms either may or may not be present in the arylene group, arylalkylene group, alkylarylene groups, the arylene group, arylalkylene group, alkylarylene group containing from about 7 to about 20 carbon atoms, such as from about 7 to about 18 carbon atoms, or from about 7 to about 14 carbon atoms; and the $R_2$-$R_{25}$ groups are independently selected from the group consisting of hydrogen, alkyl groups, arylalkyl groups, alkylaryl groups, and heterocyclic groups; and wherein $(CH_2)x$ denotes one or more methylene groups, x is an integer of from 1 to about 36, such as an integer of from 1 to about 24, or an integer of from about 1 to about 20.

In embodiments, the R group, such as one or more of $R_2$-$R_{25}$ groups of the general formulas of the present disclosure, may be the same or different from each other. Unless designated otherwise, this concept applies to all formulas of the present disclosure. General Formula I may be used for an exemplary illustration of this concept. For example, one or more of the $R_2$-$R_{25}$ groups in General Formula I may be identical. Alternatively, in embodiments, one or more of the $R_2$-$R_{25}$ groups in General Formula I may be different.

The compounds of the above General Formulas may be prepared by a condensation reaction between the suitable diacid and a suitable amount of a desired alcohol. In embodiments, the reactions may be performed at a reduced pressure (in a solvent-less process or in the presence of a solvent), such as less than about 100 mmHg, or in the range of from about 0.1 mmHg to about 50 mmHg. In embodiments, the reactions may be performed in a solvent-less process, or in the presence of a solvent, at a suitable temperature to achieve the desired degree of completion of the reaction, such as in the temperature range of from about 110° C. to about 230° C., or from about 130° C. to about 220° C., or from about 150° C. to about 210° C. In embodiments, the condensation reaction may be carried out with or without the use of a catalyst (in a solvent-less process or in the presence of a solvent); however catalysts may be used to expedite the completion of the reaction. The various types of catalysts that can be used include, for example, tetraalkyl titanates, dialkyltin oxides such as dibutyltin oxide (dibutyl oxostannane), tetraalkyltin oxide compounds such as dibutyltin dilaurate, dialkylstannoic acid compounds such as butylstannoic acid, aluminum alkoxides, alkyl zinc, dialkyl zinc, zinc oxide, stannous oxide, titanium dioxide or mixtures thereof; and which catalysts are selected in amounts of, for example, from about 0.005 weight percent to about 5 weight percent based on the starting diacid. In embodiments, the condensation reaction is complete (i.e., at least 95%, such as 99%, of the diacid has been reacted) in less than about 24 hours, such as less than about 20 hours, or less than about 15 hours.

As an example, in General Scheme 1 (below) an exemplary alcohol (such as ABITOL E™ (available from Eastrman Chemical) is utilized as a starting reagent. ABITOL E is shown by a representative structure, and comprises hydroabietyl alcohol (CAS[13393-93-6]), methyl ester of hydrogenated rosin (CAS[8050-15-5]), and decarboxylated rosin (CAS[8050-18-8])) is reacted with a di-acid to give a mixture of di-esters and monoesters depending on the reaction conditions, where R of the di-acid may be defined as set forth above with respect to $R_1$ of General Formula I.

General Scheme 1

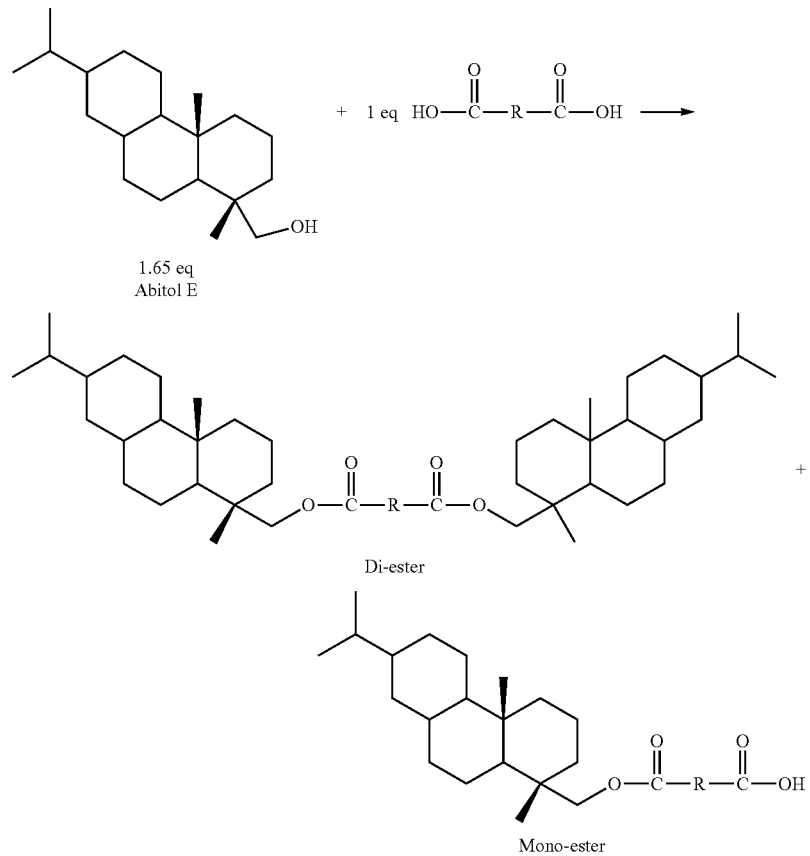

The product can be used without any purification. This is the preferred process where the reaction is done with no solvent and no further purification. Solvent free reactions are good for the environment and also cost effective.

The mono-ester can be present in the product in about 1% to about 50% compared to the di-ester, or from about 1.5% to about 40%.

In a specific embodiment, the composition of the present disclosure comprises at least one ester compound represented by General Formulas III and/or IV:

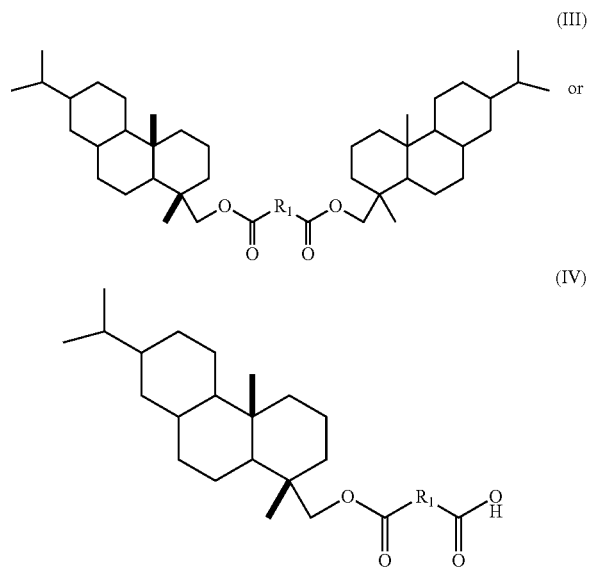

or a mixture of one or more compounds of General Formulas III and/or IV; where $R_1$ is defined as above (for General Formula I), namely: (a) an alkylene group, including substituted and unsubstituted alkylene groups, wherein hetero atoms either may or may not be present in the alkylene group; (b) an arylene group, including substituted and unsubstituted arylene groups, wherein hetero atoms either may or may not be present in the arylene group; (c) an arylalkylene group, including substituted and unsubstituted arylalkylene groups, wherein hetero atoms either may or may not be present in either or both of the alkyl portion and the aryl portion of the arylalkylene group; or (d) an alkylarylene group, including substituted and unsubstituted alkylarylene groups, wherein hetero atoms either may or may not be present in either or both of the alkyl portion and the aryl portion of the alkylarylene group; wherein two or more substituents can be joined together to form a ring.

In embodiments, the ester product of the reaction of the diacid and alcohol is biodegradable and/or the diacid and/or alcohol is selected to be derived from a renewable resource. Products can be tested for whether they are sourced from petroleum or from renewable resources by $^{14}C$ radiocarbon dating. Products sourced from petroleum will have substantially high $^{14}C$ radiocarbon dating values, in the millions of years, compared to very recent or present day radiocarbon values for those products derived from renewable resources. Examples of suitable bio-renewable di-acids include malic acid, tartaric acid, succinic acid, itaconic acid, azelaic acid, which are derived from agricultural and forestry sources. In this manner, the entire ester resin or compound may be selected to be bio-renewable, or more sustainable.

Specific examples of resin esters include but are not limited to the structures shown below:

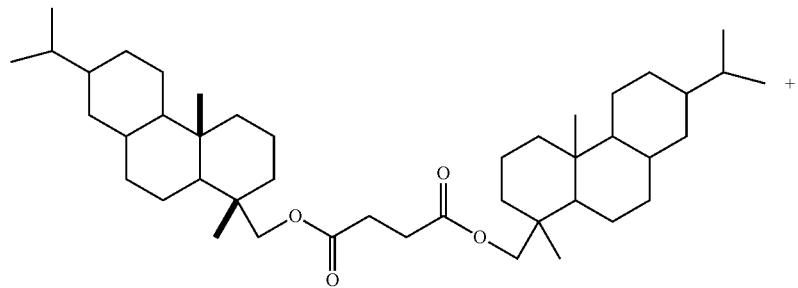

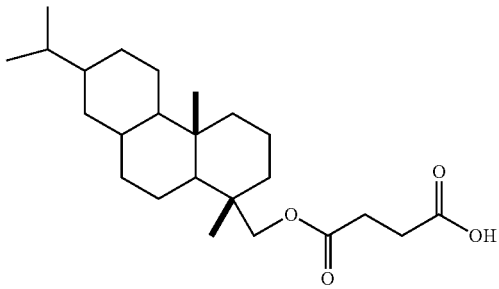

-continued
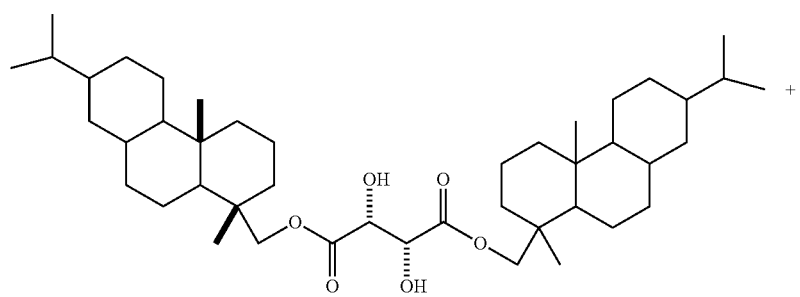
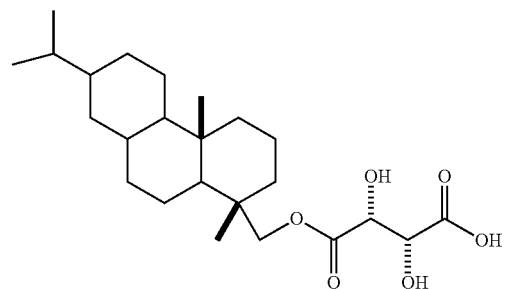
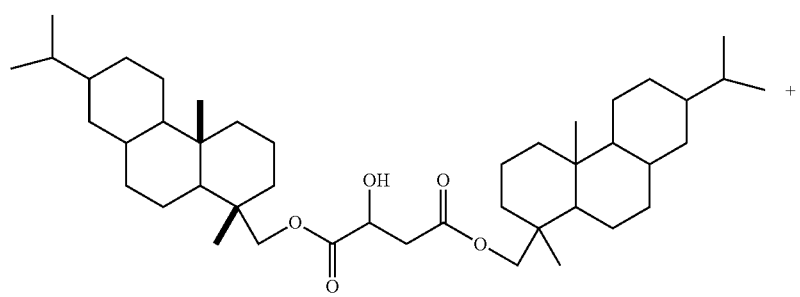
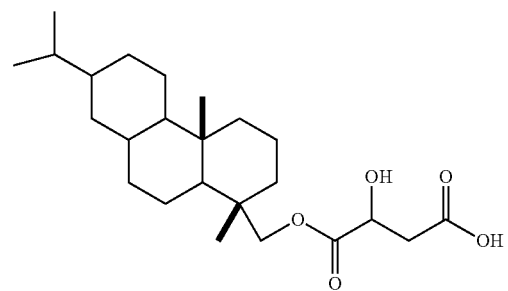
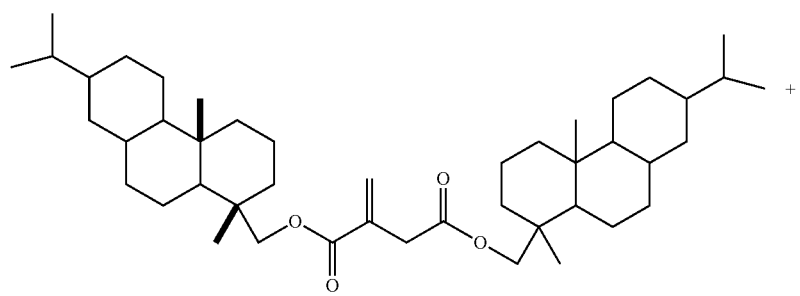

-continued

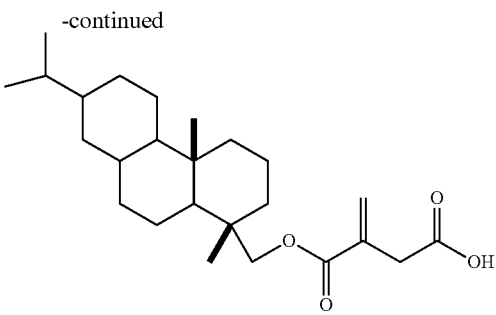

The bio-renewable ester resin or compound may be present in the composition, such as ink carrier, in any desired or effective amount, such as in an amount of from at least about 40 percent by weight, or at least about 35 percent by weight, and or at least about 30 percent by weight, and/or no less than about 5 percent by weight.

In embodiments, the sources components of the composition, such as ink carrier contents sources, may be selected such that the composition can have a high bio-renewable content (BRC). For example, for an ink composition, rosin alcohol, Abitol E derived from pine sap can be reacted with di-acids, such as succinic, itaconic, and azelaic acid, which are 100% BRC to form an amorphous binder agent for the ink composition of the present disclosure. Such an ink may also contain a crystalline phase change agent. Possible crystalline components may include trans-cinnamic acid derivatives such as the ones described in U.S. application Ser. No. 13/196,227; entitled "Phase Change Inks Containing Crystalline Trans-Cinnamic Diesters and Amorphous Isosorbide Oligomers," with the named inventors Adela Goredema et. al. the disclosures of which are incorporated herein by reference in its entirety. Trans-cinnamic acid is a natural material found in oil of cinnamon, or in balsams such as storax or shea butter. Trans-cinnamic acid can also be derived from the natural amino-acid phenylalanine using the enzyme phenyalanine ammonia-lyase. Such an ink may comprise crystalline trans-cinnamic diesters having a general formula

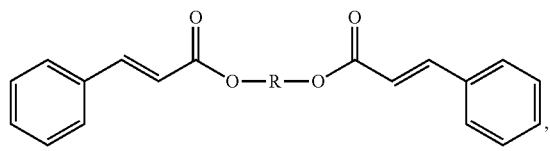

wherein R is:
(a) an alkylene group, including substituted and unsubstituted alkylene groups, and wherein hetero atoms either may or may not be present in the alkylene group;
(b) an arylene group, including substituted and unsubstituted arylene groups, and wherein hetero atoms either may or may not be present in the arylene group;
(c) an arylalkylene group, including substituted and unsubstituted arylalkylene groups, and wherein hetero atoms either may or may not be present in either or both of the alkyl portion and the aryl portion of the arylalkylene group; or
(d) an alkylarylene group, including substituted and unsubstituted alkylarylene groups, and wherein hetero atoms either may or may not be present in either or both of the alkyl portion and the aryl portion of the alkylarylene group;
wherein two or more substituents can be joined together to form a ring.

Specific examples of suitable trans-cinnamic acid derived diesters include (but are not limited to) propane-1,3-trans-cinnamate, of the formulas,

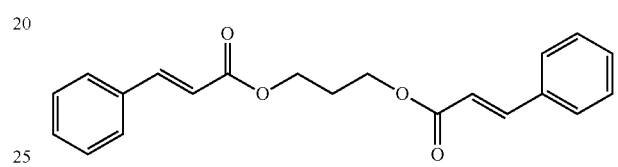

butane-1,4-trans-cinnamate, of the formula

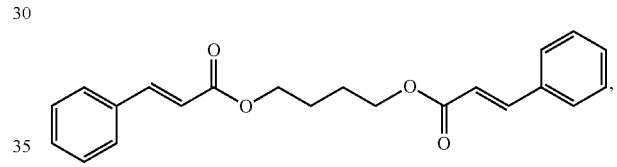

hexane-1,6-trans-cinnamate, of the formula

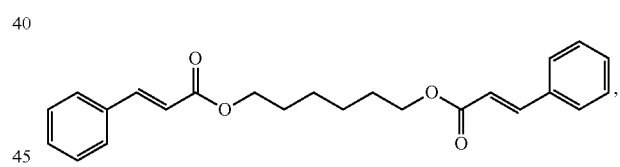

trans-cyclohexane-1,4-dimethanol-trans-cinnamate, of the formula

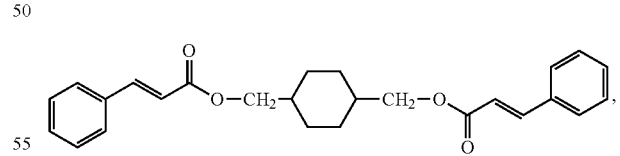

para-phenyl-1,4-dimethanol-trans-cinnamate, of the formula

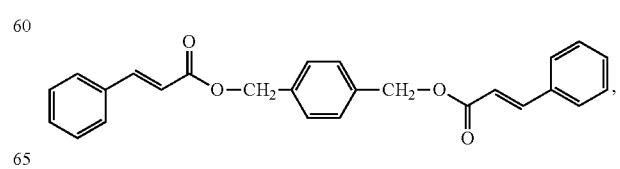

bis(hydroxymethyl)furan-trans-cinnamate, of the formula

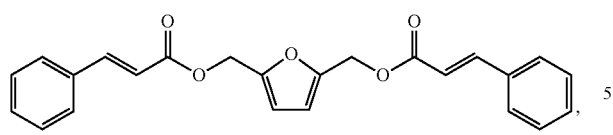

2,5-dihydroxymethyl-tetrahydrofuran-trans-cinnamate, of the formula

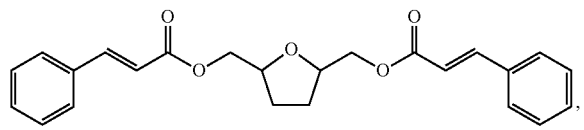 [SMILES: O=C(/C=C/c1ccccc1)OCC1CCC(COC(=O)/C=C/c2ccccc2)O1]

trans-cinnamic acid-2,3-butanediol diester, of the formula

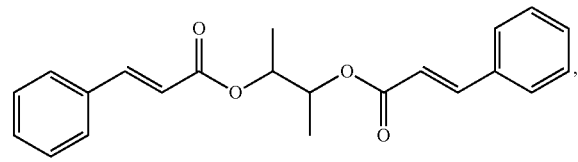 [SMILES: CC(OC(=O)/C=C/c1ccccc1)C(C)OC(=O)/C=C/c1ccccc1]

and the like, as well as mixtures thereof.

In one specific embodiment, the diol is selected to be derived from a renewable resource. Products can be tested for whether they are sourced from petroleum or from renewable resources by $^{14}C$ radiocarbon dating. Products sourced from petroleum will have substantially high $^{14}C$ radiocarbon dating values, in the millions of years, compared to very recent or present day radiocarbon values for those products derived from renewable resources. Examples of suitable bio-renewable diols include, but are not limited to, 1,4-butanediol, 1,3-propanediol, 2,3-butanediol, and the like, which can be obtained from sugars. In this manner, the entire trans-cinnamic diester material can be selected to be bio-renewable.

In embodiments where the composition is an ink, other possible crystalline phase change agents may include tartaric acid di-esters such as the ones described in U.S. patent application Ser. No. 13/095,715; entitled "Solid Ink Compositions Comprising Crystalline Esters of Tartaric Acid" to Kentaro Morimitsu et al., the disclosure of which is incorporated herein by reference in its entirety. The crystalline component being a di-ester having a general formula of

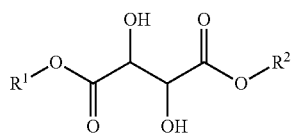

wherein $R^1$ and $R^2$ each, independently of the other or meaning that they can be the same or different is derived from alcohols $R^1$—OH and $R^2$—OH, selected from the group consisting of

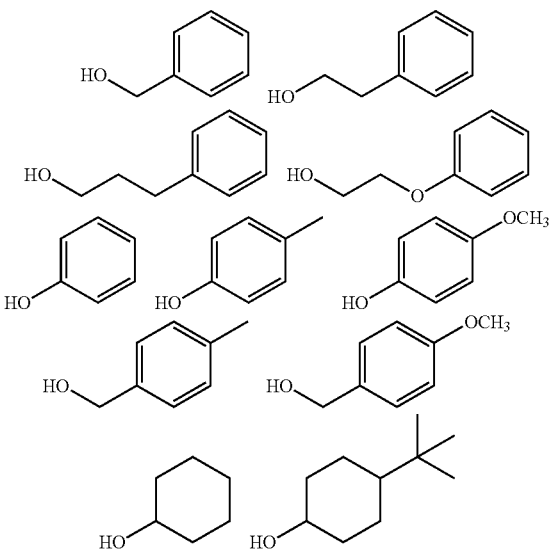

and mixtures thereof, and wherein the tartaric acid backbone is selected from L-(+)-tartaric acid, D-(−)-tartaric acid, DL-tartaric acid, or mesotartaric acid, and mixtures thereof.

Other possible crystalline phase change agents may include diurethanes such as the ones described in U.S. patent application Ser. No. 13/456,619; entitled "Phase change ink compositions comprising crystalline diurethanes and derivatives thereof" to Naveen Chopra et al., the disclosure of which is incorporated herein by reference in its entirety. The crystalline component being a diurethane having a general formula of

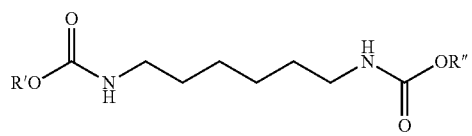

wherein each R' and R" of the diurethane is independently selected from benzyl, 2-phenylethyl, 2-phenoxyethyl, $C_6H_5$(CH$_2$)$_4$-, cyclohexyl, 2-methylcyclohexyl, 3-methylcyclohexyl, 4-methylcyclohexyl, cyclohexylmethyl, 2-methylcyclohexylmethyl, 3-methylcyclohexylmethyl and 4-methylcyclohexylmethyl.

In embodiments, the composition includes an ink carrier (defined as that portion of the ink other than the colorant and other minor additives such as antioxidants and the like) that has a BRC of at least about 5%, such as at least about 10%, or at least about 15% by weight of the ink carrier. In such embodiments, both the crystalline phase change agent, such as a crystalline trans-cinnamic diester, and the amorphous and the esters resin or compound of the present disclosure (such as a compound of General Formula I and II), are a class of materials known to be readily biodegradable, further enhancing the environmental sustainability of the ink.

In embodiments, the ester resins, such as Abitol E ester resins or compounds (e.g., one or more ester resin or compound having the general structure of General Formulas I-IV), may be present in an amount of from about 5% to about 40%, or from about 10% to about 35%, or from about 15% to about 30% by weight, such as by weight of the phase-change ink composition. In embodiments, the ester resins, such as Abitol E ester resins or compounds, of the present disclosure may be incorporated into colored or non-colored (or colorless) phase-change ink compositions that include from about 0.5 to about 10%, or from about 1 to about 8%, or from about 2 to about 5% by weight of dye or pigment.

In embodiments, the composition may be an ink composition that may contain at least two different ester resins, such as Abitol E ester resins or compounds in any desired amount, which may function as the binder agent, wherein the weight-percent ratio between a crystalline phase-change agent and the binder agent (such as an ester resin) may be from about 95:5 to about 60:40, such as from about 90:10 to about 70:30.

In embodiments, such an ink composition may comprise a colorant; a crystalline phase-change agent, and an amorphous binder agent or resin, wherein the ink includes one or more ester resins, such as Abitol E ester resins or compounds. In specific embodiments, the ink composition may be a solid at from about 20° C. to about 60° C. In embodiments, the composition may be a phase change ink, where the phase change inks can be solid inks which have melting points of from about 65° C. to about 150° C., for example from about 66° C. to about 145° C., from about 70° C. to about 140° C., as determined, for example, by differential scanning calorimetry. In embodiments, the phase change ink has a crystallization point of from about 65° C. to about 120° C., or from about 60 to about 115° C.

In further embodiments, the composition may be a phase change ink, where the phase change inks can have a complex viscosity in the molten state, such as for example temperatures above 130° C. in the range of from about 1 to about 20 cPs (centipoise, or mPa-sec), or from about 2 to about 18 cPs, or from about 3 to about 15 cPs. The complex viscosities of the phase change ink can be measured at a range of frequencies, such as from about 1 Hz to about 100 Hz. At room temperature, the phase change ink can have a complex viscosity of about $\geq 1 \times 10^6$ cPs.

The composition, such as an ink composition, of embodiments may further include conventional additives to take advantage of the known functionality associated with such conventional additives. Such additives may include, for example, at least one antioxidant, defoamer, slip and leveling agents, clarifiers, viscosity modifiers, adhesive or tackifiers, plasticizers and the like.

The compositions of embodiments, which may be incorporated into ink(s) or coatings, may further include conventional additives to take advantage of the known functionality associated with such additives. Such optional additives may include, for example, an antioxidant, defoamer, UV absorber, slip and leveling agents, synergists, adjuvants, clarifier, tackifier, adhesive, plasticizer and the like.

In embodiments, the composition, such as an ink composition, may optionally contain antioxidants to protect the images from oxidation and also may protect the components, such as the ink components, from oxidation while existing as a heated melt in the ink reservoir. Examples of suitable antioxidants include (1) N,N'-hexamethylene bis(3,5-di-tert-butyl-4-hydroxy hydrocinnamamide) (IRGANOX 1098, available from Ciba Inc.), (2) 2,2-bis(4-(2-(3,5-di-tert-butyl-4-hydroxyhydrocinnamoyloxy))ethoxyphenyl) propane (TOPANOL-205, available from ICI America Corporation), (3) tris(4-tert-butyl-3-hydroxy-2,6-dimethyl benzyl) isocyanurate (CYANOX 1790, 41,322-4, LTDP, Aldrich D12,840-6), (4) 2,2'-ethylidene bis(4,6-di-tert-butylphenyl) fluoro phosphonite (ETHANOX-398, available from Ethyl Corporation), (5) tetrakis(2,4-di-tert-butylphenyl)-4,4'-biphenyl diphosphonite (ALDRICH 46,852-5; hardness value 90), (6) pentaerythritol tetrastearate (TCI America #PO739), (7) tributylammonium hypophosphite (Aldrich 42,009-3), (8) 2,6-di-Cert-butyl-4-methoxyphenol (Aldrich 25,106-2), (9) 2,4-di-tert-butyl-6-(4-methoxybenzyl) phenol (Aldrich 23,008-1), (10) 4-bromo-2,6-dimethylphenol (Aldrich 34,951-8), (11) 4-bromo-3,5-didimethylphenol (Aldrich B6,420-2), (12) 4-bromo-2-nitrophenol (Aldrich 30,987-7), (13) 4-(diethyl aminomethyl)-2,5-dimethylphenol (Aldrich 14,668-4), (14) 3-dimethylaminophenol (Aldrich D14,400-2), (15) 2-amino-4-tert-amylphenol (Aldrich 41,258-9), (16) 2,6-bis(hydroxymethyl)-p-cresol (Aldrich 22,752-8), (17) 2,2'-methylenediphenol (Aldrich B4,680-8), (18) 5-(diethylamino)-2-nitrosophenol (Aldrich 26,951-4), (19) 2,6-dichloro-4-fluorophenol (Aldrich 28,435-1), (20) 2,6-dibromo fluoro phenol (Aldrich 26,003-7), (21) α-trifluoro-o-creso-1 (Aldrich 21,979-7), (22) 2-bromo-4-fluorophenol (Aldrich 30,246-5), (23) 4-fluorophenol (Aldrich F1,320-7), (24) 4-chlorophenyl-2-chloro-1,1,2-tri-fluoroethyl sulfone (Aldrich 13,823-1), (25) 3,4-difluoro phenylacetic acid (Aldrich 29,043-2), (26) 3-fluorophenylacetic acid (Aldrich 24,804-5), (27) 3,5-difluoro phenylacetic acid (Aldrich 29,044-0), (28) 2-fluorophenylacetic acid (Aldrich 20,894-9), (29) 2,5-bis(trifluoromethyl)benzoic acid (Aldrich 32,527-9), (30) ethyl-2-(4-(4-(trifluoromethyl) phenoxy) phenoxy) propionate (Aldrich 25,074-0), (31) tetrakis(2,4-di-tert-butyl phenyl)-4,4'-biphenyl diphosphonite (Aldrich 46,852-5), (32) 4-tert-amyl phenol (Aldrich 15,384-2), (33) 3-(21'-benzotriazol-2-yl)-4-hydroxy phenethylalcohol (Aldrich 43,071-4), NAUGARD 76, NAUGARD 445, NAUGARD 512, AND NAUGARD 524 (manufactured by Chemtura Corporation), and the like, as well as mixtures thereof. The antioxidant, when present, may be present in the composition in any desired or effective amount, such as from about 0.25 percent to about 10 percent by weight or from about 0.5 percent to about 5 percent by weight of the composition.

The ink compositions of the present disclosure may further contain an optional tackifier such as the commercial derivatives of rosin acids derived from gum rosins or tall oil resins. Representative examples include, but are not limited to, a glycerol ester of hydrogenated abietic (rosin) acid such as FORAL 85 (commercially available from Eastman), or a pentaerythritol ester of hydroabietic (rosin) acid such as FORAL 105 (commercially available from Eastman), or CELLOLYN 21, a hydroabietic (rosin) alcohol ester of phthalic acid (commercially available from Eastman), or triglycerides of hydrogenated abietic (rosin) acid such as KE-311 and KE-100 resins, (commercially available from Arakawa Chemical Industries, Ltd.), synthetic polyterpene resins such as NEVTAC 2300, NEVTAC 100, and NEVTACO 80 (commercially available from Neville Chemical Company), WINGTACK 86, a modified synthetic polyterpene resin (commercially available from Sartomer), and the like. Tackifiers may be present in the ink in any effective amount, such as from about 0.01 percent by weight of the ink to from about 30 percent by weight of the ink, from about 0.1 percent by weight of the ink to about 25 percent by weight of the ink, from about 1 weight percent of the ink to about 20 weight percent of the ink.

Plasticizers such as UNIPLEX 250 (commercially available from Unitex), the phthalate ester plasticizers commercially available from Ferro under the trade name SANTICIZER, such as dioctyl phthalate, diundecyl phthalate, alkylbenzyl phthalate (SANTICIZER 278), triphenyl phosphate (commercially available from Ferro), KP-140, a tributoxyethyl phosphate (commercially available from Great Lakes Chemical Corporation), MORFLEX 150, a dicyclohexyl phthalate (commercially available from Morflex Chemical Company Inc.), trioctyl trimellitate (commercially available from Sigma Aldrich Co.), and the like. Plasticizers may be present in an amount from about 0.01 to about 30 percent, from about 0.1 to about 25 percent, from about 1 to about 20 percent by weight of the ink.

In embodiments, the compositions, such as ink compositions, described herein also include at least one colorant. Any desired or effective colorant can be employed in the ink compositions, including dyes, pigments, mixtures thereof, and the like, provided that the colorant can be dissolved or dispersed in the ink carrier. Any dye or pigment may be chosen, provided that it is capable of being dispersed or dissolved in the ink carrier and is compatible with the other ink components. The ink compositions can be used in combination with conventional ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Ciba); Direct Brilliant Pink B (Oriental Giant Dyes); Direct Red 3BL (Classic Dyestuffs); Supranol Brilliant Red 3BW (Bayer AG); Lemon Yellow 6G (United Chemie); Light Fast Yellow 3G (Shaanxi); Aizen Spilon Yellow C-GNH (Hodogaya Chemical); Bernachrome Yellow GD Sub (Classic Dyestuffs); Cartasol Brilliant Yellow 4GF (Clariant); Cibanon Yellow 2GN (Ciba); Orasol Black CN (Ciba); Savinyl Black RLSN (Clariant); Pyrazol Black BG (Clariant); Morfast Black 101 (Rohm & Haas); Diaazol Black RN (ICI); Orasol Blue GN (Ciba); Savinyl Blue GLS (Clariant); Luxol Fast Blue MBSN (Pylam Products); Sevron Blue 5GMF (Classic Dyestuffs); Basacid Blue 750 (BASF), Neozapon Black X51 (BASF), Classic Solvent Black 7 (Classic Dyestuffs), Sudan Blue 670 (C.I. 61554) (BASF), Sudan Yellow 146 (C.I. 12700) (BASF), Sudan Red 462 (C.I. 26050) (BASF), C.I. Disperse Yellow 238, Neptune Red Base NB543 (BASF, C.I. Solvent Red 49), Neopen Blue FF-4012 from BASF, Lampronol Black BR from ICI (C.I. Solvent Black 35), Morton Morplas Magenta 36 (C.I. Solvent Red 172), metal phthalocyanine colorants such as those disclosed in U.S. Pat. No. 6,221,137, the disclosure of which is totally incorporated herein by reference, and the like. Other suitable dyes include those disclosed in U.S. Patent Application Publication No. 2010/0086683 and U.S. Pat. Nos. 7,732,581; 7,381,831; 6,713,614; 6,646,111; 6,590,082; 6,472,523; 6,713,614; 6,958,406; 6,998,493; 7,211,131; and 7,294,730, each of which is incorporated herein by reference in its entirety. Polymeric dyes can also be used, such as those disclosed in, for example, U.S. Pat. No. 5,621,022 and U.S. Pat. No. 5,231,135, the disclosures of each of which are herein entirely incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, Solvent Yellow 162, Acid Red 52, Solvent Blue 44, and uncut Reactant Violet X-80.

In embodiments, solvent dyes are employed. Examples of suitable solvent dyes include Neozapon Red 492 (BASF); Orasol Red G (Ciba); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow CGP (Ciba); Orasol Black RLP (Ciba); Savinyl Black RLS (Clariant); Morfast Black Conc. A (Rohm and Haas); Orasol Blue GN (Ciba); Savinyl Blue GLS (Sandoz); Luxol Fast Blue MBSN (Pylam); Sevron Blue 5GMF (Classic Dyestuffs); Basacid Blue 750 (BASF), Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 260501] (BASF), mixtures thereof and the like.

Pigments are also suitable colorants for the ink composition described herein. Examples of suitable pigments include PALIOGEN Violet 5100 (commercially available from BASF); PALIOGEN Violet 5890 (commercially available from BASF); HELIOGEN Green L8730 (commercially available from BASF); LITHOL Scarlet D3700 (commercially available from BASF); SUNFAST Blue 15:4 (commercially available from Sun Chemical); Hostaperm Blue B2G-D (commercially available from Clariant); Hostaperm Blue B4G (commercially available from Clariant); Permanent Red P-F7RK; Hostaperm Violet BL (commercially available from Clariant); LITHOL Scarlet 4440 (commercially available from BASF); Bon Red C (commercially available from Dominion Color Company); ORACET Pink RF (commercially available from Ciba); PALIOGEN Red 3871K (commercially available from BASF); SUNFAST Blue 15:3 (commercially available from Sun Chemical); PALIOGEN Red 3340 (commercially available from BASF); SUNFAST Carbazole Violet 23 (commercially available from Sun Chemical); LITHOL Fast Scarlet L4300 (commercially available from BASF); SUNBRITE Yellow 17 (commercially available from Sun Chemical); HELIOGEN Blue L6900, L7020 (commercially available from BASF); SUNBRITE Yellow 74 (commercially available from Sun Chemical); SPECTRA PAC C Orange 16 (commercially available from Sun Chemical); HELIOGEN Blue K6902, K6910 (commercially available from BASF); SUNFAST Magenta 122 (commercially available from Sun Chemical); HELIOGEN Blue D6840, D7080 (commercially available from BASF); Sudan Blue OS (commercially available from BASF); NEOPEN Blue FF4012 (commercially available from BASF); PV Fast Blue B2GO1 (commercially available from Clariant); IRGALITE Blue BCA (commercially available from Ciba); PALIOGEN Blue 6470 (commercially available from BASF); Sudan Orange G (commercially available from Aldrich), Sudan Orange 220 (commercially available from BASF); PALIOGEN Orange 3040 (BASF); PALIOGEN Yellow 152, 1560 (commercially available from BASF); LITHOL Fast Yellow 0991K (commercially available from BASF); PALIOTOL Yellow 1840 (commercially available from BASF); NOVOPERM Yellow FGL (commercially available from Clariant); Ink Jet Yellow 4G VP2532 (commercially available from Clariant); Toner Yellow HG (commercially available from Clariant); Lumogen Yellow D0790 (commercially available from BASF); Suco-Yellow L1250 (commercially available from BASF); Suco-Yellow D1355 (commercially available from BASF); Suco Fast Yellow D1 355, D1 351 (commercially available from BASF); HOSTAPERM Pink E 02 (commercially available from Clariant); Hansa Brilliant Yellow 5GX03 (commercially available from Clariant); Permanent Yellow GRL 02 (commercially available from Clariant); Permanent Rubine L6B 05 (commercially available from Clariant); FANAL Pink D4830 (commercially available from BASF); CINQUASIA Magenta (commercially available from DU PONT); PALIOGEN Black L0084 (commercially available from BASF); Pigment Black K801 (commercially available from BASF); and carbon blacks such as REGAL 330™ (commercially available from Cabot), Nipex 150 (commercially available from Degusssa) Carbon Black 5250 and Carbon Black 5750 (commercially available from Columbia Chemical), and the like, as well as mixtures thereof. Other suitable pigments include those disclosed in U.S. Pat. Nos. 7,905,954; 7,503,973; 7,465,348; and 7,427,323.

When present, the optional additives may each, or in combination, be present in the composition in any desired or effective amount, such as from about 0.1 to about 15 percent or from about 0.5 to about 12 percent by weight of the composition.

The amount of colorant in the composition, such as a phase-change ink, of the present disclosure, may be from about 0.5% to about 20% or from about 1% to about 15% by weight, or from about 2% to about 10% by weight of the composition.

The compositions, such as ink compositions, can be prepared by any desired or suitable method. For example, for an ink composition, each of the components of the ink carrier can be mixed together, followed by heating, the mixture to at least its melting point, for example from about 60 to about 150° C., such as from about 80 to about 140° C., or from about 85 to about 120° C.

The compositions, such as ink compositions, can be employed in an apparatus for use, such as for an ink jet printing process either directly to paper, or indirectly to an intermediate transfer member. Examples of apparatuses that are suitable for printing the phase-change inks described herein include apparatuses comprised of at least one thermally controlled ink retaining reservoir to store or hold molten phase-change ink, an ink jet head for printing the ink, and an ink supply line for providing the phase-change ink to the ink jet head.

Another embodiment disclosed herein is directed to a process which comprises incorporating the composition, such as ink composition, as disclosed herein into an ink jet printing apparatus, melting the ink, and causing droplets of the melted ink to be ejected in an imagewise pattern onto a recording substrate. Known direct printing process may be suitable for applying the ink compositions of the present disclosure onto a substrate.

Yet another embodiment disclosed herein is directed to a process which comprises incorporating an composition, such as an ink composition, as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. In another specific embodiment, both the intermediate transfer member and the final recording sheet are heated; in this embodiment, both the intermediate transfer member and the final recording sheet are heated to a temperature below that of the melted ink in the printing apparatus; in this embodiment, the relative temperatures of the intermediate transfer member and the final recording sheet can be (1) the intermediate transfer member is heated to a temperature above that of the final recording substrate and below that of the melted ink in the printing apparatus; (2) the final recording substrate is heated to a temperature above that of the intermediate transfer member and below that of the melted ink in the printing apparatus; or (3) the intermediate transfer member and the final recording sheet are heated to approximately the same temperature. An offset or indirect printing process is also disclosed in, for example, U.S. Pat. No. 5,389,958, the disclosure of which is incorporated herein by reference. In one specific embodiment, the printing apparatus employs a piezoelectric printing process wherein droplets of the ink are caused to be ejected in imagewise pattern by oscillations of piezoelectric vibrating elements. Inks as disclosed herein can also be employed in other hot melt printing processes, such as hot melt acoustic ink jet printing, hot melt thermal ink jet printing, hot melt continuous stream or deflection ink jet printing, and the like. Phase-change inks as disclosed herein can also be used in printing processes other than hot melt ink jet printing processes, such as hot-melt lithographic, flexographic, and related offset ink printing processes.

Any suitable substrate or recording sheet can be employed such as plain paper, coated paper stocks and heavy paper stocks, transparency materials, fabrics, textile products, plastics, flexible polymeric films, inorganic substrates such as metals or silicon wafers, wood, and the like.

The compositions described herein are further illustrated in the following examples. All parts and percentages are by weight unless otherwise indicated.

EXAMPLES

Example 1

Synthesis of Abitol E Succinate (Compound 1, Table 1)

Into a 3 neck 100 mL round bottomed flask equipped with a dean stark trap and condenser, thermocouple and argon inlet was added: Abitol E (40 grams, available from Eastman Chemical), Succinic Acid (8.07 grams, available from Sigma Aldrich), and Fascat 4100 (0.05 grams, available from Arkema Inc,). The mixture was slowly heated under argon to 180° C. during which all the reagents melted. The reaction mixture was stirred at 180° C. for about 12 hours during which about 1 mL water was collected in dean stark trap. A vacuum was applied (1-2 mm-Hg) for approximately 15 minutes to give an additional 0.5 mL of water. The reaction was cooled under argon to approximately 120° C. and discharged in an aluminum tray and then cooled to room temperature to give 40 grams of a tacky off-white solid. The tacky off-white solid was dissolved in dichloromethane (approximately 150 mL) and washed with $NaHCO_3$ (2×100 mL). The organic layer was then washed with water (2×100 mL), dried with $MgSO_4$, then rotavoped to remove solvent and dried on vacuum pump (overnight) to give a tacky solid. Physical properties of this compound are shown in Table 1.

Example 2

Synthesis of Abitol E Succinate (Compound 2, Table 1)

Into a 1 neck 250 mL round bottomed flask equipped with a dean stark trap, condenser and argon inlet was added: Abitol E (20 grams, available from Eastman Chemical), Succinic Acid (4.06 grams, available from Sigma Aldrich), p-toluenesulphonic acid (0.12 grams, available from Sigma Aldrich) and Toluene (180 mL). The mixture was allowed to reflux overnight (approximately 20 hours) during which 0.5 mL water was collected. The mixture was cooled to room temperature during which unreacted succinic acid precipitated out. Then the mixture was heated again and distilled out all the toluene, added Xylenes (150 mL) and refluxed overnight (20 hours) during which another 0.2 mL water was collected. The mixture was then rotavoped to remove the solvent to give a gummy solid, which was dissolved in dichloromethane (approximately 150 mL) and washed with $NaHCO_3$ (2×100 mL). Next the organic layer was washed with water (2×100 mL), dried with $MgSO_4$, and then rotavoped to remove solvent and dried on vacuum pump overnight to give a tacky solid. Physical properties of this compound are shown in Table 1.

Example 3

Synthesis of Abitol E Tartarate (Compound 3, Table 1)

Compound 3 was prepared using the same procedure as in Example 2 except only Xylenes were used as solvent from the beginning. Physical properties of this compound are shown in Table 1.

TABLE 1

Physical properties of Ester Resin binders

| Compound No. | R | Process | Acid Value | Tg midpoint (°C.) | Viscosity at 140° C. (cps) | *MALDI-ToF Analysis % Diester | *MALDI-ToF Analysis % Monoester |
|---|---|---|---|---|---|---|---|
| 1 | —CH$_2$CH$_2$— | Neat | 19 | 6 | 37.8 | 63 | 37 |
| 2 | —CH$_2$CH$_2$— | Toluene & Xylene reflux | 6.6 | 6 | 33 | 86 | 14 |
| 3 | —CH(OH)CH(OH)— | Xylene reflux | 3.8 | 21 | 53.5 | 82 | 13 |

*MALDI-ToF refers to Matrix-Assisted Laser Desorption/Ionization Time of Flight Mass Spectrometry
Note:
Compound number 3 had about 5% starting material left.

Ink Example 1

Preparation of Phase Change Ink

Into a 30 mL amber bottle was charged, in the following order: 3.92 grams of a crystalline phase change agent (1,4-butanediol-di-cinnamate; 78.4 weight percent; described in Ser. No. 13/196,227 and 0.98 g of Abitol E binder (Compound 1 of Table 1, 19.6 weight percent). The materials were melted at 140° C. and stirred using a magnetic stir bar for 30 minute after which was added 0.1 gram Keyplast Solvent blue 101 dye (2 weight percent, purchased from Keystone) to the molten mixture. The ink was stirred for an additional 1 hour at 140° C., poured in an Aluminum tray and cooled to room temperature. The physical properties of the ink are shown in Table 2.

Ink Examples 2-6

These Ink Examples were prepared using the same procedure as Ink Example 1. The physical properties of these inks are shown in Table 2.

Ink Example 7

Preparation of Phase Change Ink

To a 600 mL beaker was charged 78.40 grams of Abitol E binder (Compound 1 of Table 1, 19.6 wt %) and 313.60 g of a crystalline phase change agent (1,4-butanediol-di-cinnamate; 78.4%). The materials were melted at 140° C. and stirred using a magnetic stir bar for 30 minutes, after which time 8 g of Keyplast Solvent Blue 101 (2 wt %, purchased from Keystone) was added portionwise to the molten mixture. The ink was stirred for an additional hour at 140° C., and filtered through a 1 micron Pall filter, poured in an Aluminum tray and cooled to room temperature. The physical properties of the ink are shown in Table 2.

TABLE 2

Properties of Phase Change Inks comprising Ester Resin Binders

| Component | Ink Example 1 Wt % | Ink Example 2 Wt % | Ink Example 3 Wt % | Ink Example 4 Wt % | Ink Example 5 Wt % | Ink Example 6 Wt % | Ink Example 7 Wt % |
|---|---|---|---|---|---|---|---|
| Di-phenethyl L-tartarate 42% *BRC[1] | 78.4 | 78.4 | | | | | |
| BDO Di-cinnamate 25% *BRC[2] | | | 78.4 | 78.4 | | | 78.4 |
| diBn-HDI Diurethane 0% *BRC[3] | | | | | 78.4 | 78.6 | |
| Compound 1 100% *BRC | 19.6 | | 19.6 | | 19.6 | | 19.6 |
| Compound 3; 100 *BRC) | | 19.6 | | 19.6 | | 19.6 | |
| Keystone Solvent blue 101 Dye | 2 | 2 | 2 | 2 | 2 | 2 | 2 |
| Total | 100 | 100 | 100 | 100 | 100 | 100 | 100 |
| *BRC (%) | 52 | 52 | 39 | 39 | 19.6 | 19.6 | 39 |

TABLE 2-continued

Properties of Phase Change Inks comprising Ester Resin Binders

| Component | Ink Example 1 Wt % | Ink Example 2 Wt % | Ink Example 3 Wt % | Ink Example 4 Wt % | Ink Example 5 Wt % | Ink Example 6 Wt % | Ink Example 7 Wt % |
|---|---|---|---|---|---|---|---|
| **Viscosity @ 140° C. (cPs) | 6.31 | 5.8 | 5.37 | 5.14 | 7.29 | 13.14 | 4.81 |
| Tcryst. (° C.) (by rheology) | 75 | 100 | 65 | 65 | 120 | 120 | 65 |

[1]Described in Attorney Docket No. 20101141-US-NP.
[2]Described in Attorney Docket No. 20101649-US-NP.
[3]Described in Attorney Docket No. 20103556-US-NP.
*Bio-renewable content-weight percent of bio-based materials.
**Frequency = 1 Hz; 25 mm parallel plate geometry; gap = 0.2 mm; strain % = 200%-400%, strain independent viscosities.

Complex viscosity of the ink samples was measured using an RFS3 controlled strain Rheometer (TA instruments) equipped with a Peltier heating plate and using a 25 mm parallel plate. The method used was a temperature sweep from high to low temperatures, in temperature steps of 5° C., a soak (equilibration) time of 120 seconds between each temperature and at a constant frequency of 1 Hz. The rheology data of the phase change inks of the present disclosure is shown in FIG. 1.

The rheological profiles have sharp phase changes which are required for the ink to cool fast when it hits the paper and low viscosities at jetting temperature. The crystallization temperature of the ink depends on the crystalline component used.

Example Inks 1-6 in Table 2 were each printed onto coated paper Digital Color Elite Gloss (DCEG) (120 gsm stock) using the K-proofer gravure printing plate, which was rigged with a pressure roll set at low pressure. The gravure plate temperature was set at 142° C., but the actual plate temperature was approximately 134° C. The K-proofer apparatus (manufactured by RK Print Coat Instrument Ltd., Litlington, Royston, Heris, SG8 0OZ, U.K.) is a useful printing tool to screen a variety of inks at small scale and to assess image quality on various substrates. All the six inks gave robust images that could not be easily removed from the substrates. When a scratch/gouge finger with a curved tip at an angle of about 15° from vertical, with a weight of 528 g applied, was drawn across the image at a rate of approximately 13 minis no ink was visibly removed from the image. The scratch/gouge tip is similar to a lathe round nose cutting bit with radius of curvature of approximately 12 mm.

Example Ink 7 was jetted successfully using a modified Xerox Phaser 8860 at 108° C. onto Digital Color Elite Gloss, 120 gsm (DCEG), to form robust images that could not be easily removed from the substrates.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. An ester composition comprising at least one ester compound represented by:

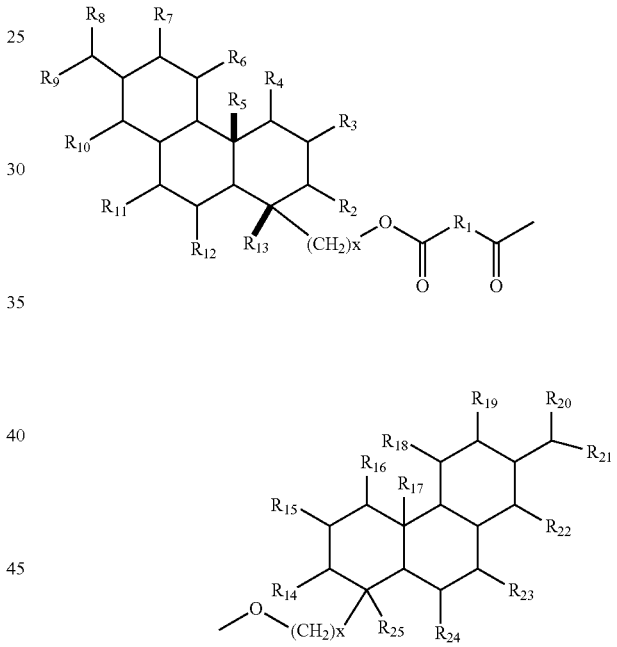

General Formula I where $R_1$ is:
an alkylene group having the structure —(CH2)p- in which p is an integer in a range of from about 2 to about 12, each of $R_2$-$R_{25}$ are independently selected from the group consisting of hydrogen, alkyl groups, arylalkyl groups, alkylaryl groups, and heterocyclic groups; and wherein x is an integer of one or more.

2. The composition of claim 1, wherein one or more of the $R_2$-$R_{25}$ groups are a methyl group and one or more of the $R_2$-$R_{25}$ groups are hydrogen.

3. The composition of claim 1, wherein x is an integer from 1 to about 20.

4. The composition of claim 1, further comprising at least one ester compound represented by General Formula III

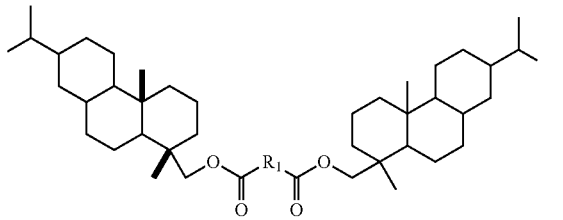

General Formula IV

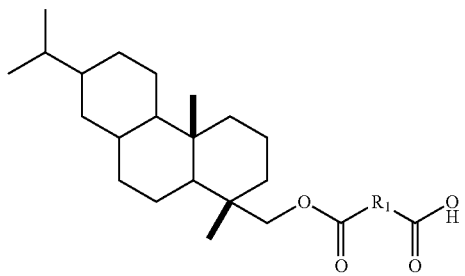

or a mixture of one or more compounds of General Formulas III and/or IV;

where $R_1$ is:
  a) an alkylene group, including substituted and unsubstituted alkylene groups, wherein hetero atoms either may or may not be present in the alkylene group;
  b) an arylene group, including substituted and unsubstituted arylene groups, wherein hetero atoms either may or may not be present in the arylene group;
  c) an arylalkylene group, including substituted and unsubstituted arylalkylene groups, wherein hetero atoms either may or may not be present in either or both of the alkyl portion and the aryl portion of the arylalkylene group; or
  d) an alkylarylene group, including substituted and unsubstituted alkylarylene groups, wherein hetero atoms either may or may not be present in either or both of the alkyl portion and the aryl portion of the alkylarylene group.

5. The composition of claim 4, wherein the composition has at least 80 percent by weight bio-renewable content, or $R_1$ is derived from a bio-renewable compound.

6. The composition of claim 5, wherein the bio-renewable compound is one or more member selected from the group consisting of succinic acid, tartaric acid, malic acid and itaconic acid.

7. The composition of claim 4 where the ester composition includes a mixture of a diester and a monoester, the mixture selected from the group consisting of:

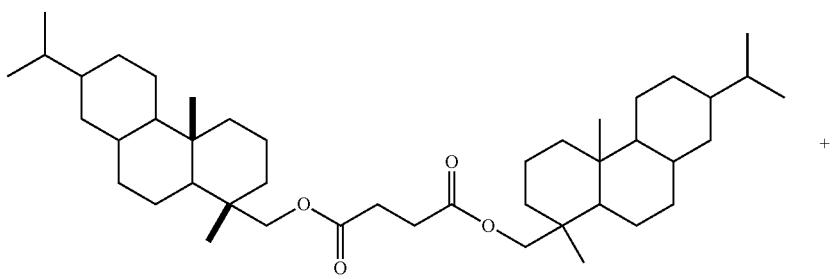

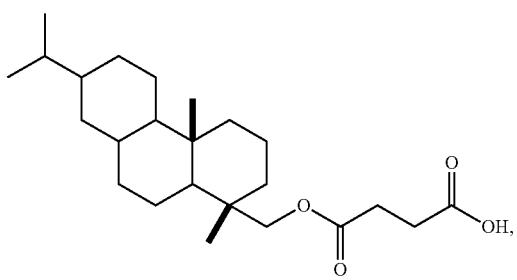

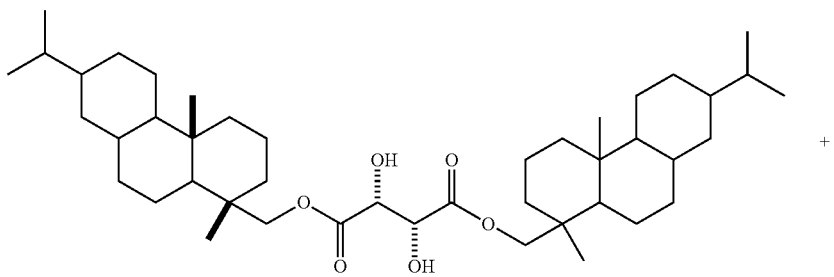

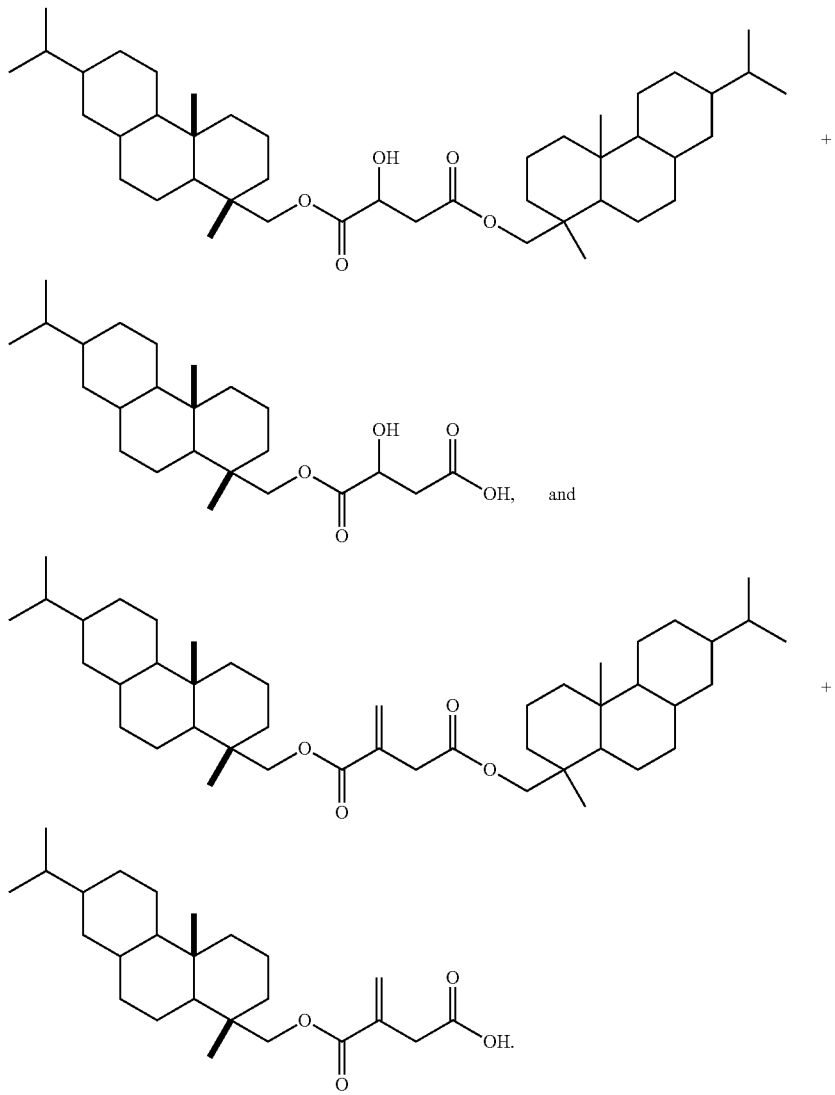

8. The composition of claim 4, wherein the ester of General Formula IV is present in the composition in an amount in the range of from about 5% to about 50% by weight of the composition.

9. The composition of claim 4, wherein the ester of General Formula III is present in the composition in an amount in the range of from about 50% to about 95% by weight of the composition.

10. A method for forming the composition of claim 4, comprising:
melting a carboxylic acid and Abitol E alcohol under an inert atmosphere in the presence of a catalyst, reacting the molten carboxylic acid and Abitol E at an elevated temperature of about 110° C. to about 230° C. under an inert atmosphere, optionally in the presence of a solvent, to form at least one ester compound, and cooling and isolating the at least one ester compound; wherein the at least one ester compound comprises one or more compound represented by General Formulas I-IV.

11. The method according to claim 10, wherein reacting the molten carboxylic acid and Abitol E to form at least one ester compound includes removing water.

12. The method according to claim 10, wherein the reaction to form the at least one ester compound occurs in a solvent selected from the group consisting of toluene, xylenes, and mesitylene.

13. The method according to claim 10, wherein the catalyst is selected from the group consisting of tetraalkyl titanates, dialkyltin oxides, dibutyltin oxide, dibutyl oxostarmane, tetraalkyltin oxide compounds, dibutyltin dilaurate, dialkylstannoic acid compounds, butylstannoic acid, aluminum alkoxides, alkyl zinc, dialkyl zinc, zinc oxide, stannous oxide, titanium oxide, p-toluenesulfonic acid, sulphuric acid, phosphoric acid, methane sulfonic acid and mixtures thereof.

14. The method according to claim 10, wherein the catalyst is present in an amount in a range of from about 0.005% to about 5% by weight based on the starting carboxylic acid.

15. The method according to claim 10, wherein the reaction to form the at least one ester compound is about 99% complete in less than about 15 hours.

16. The ester composition of claim 1, further comprising in a mixture at least one ester compound represented by:

General Formula II

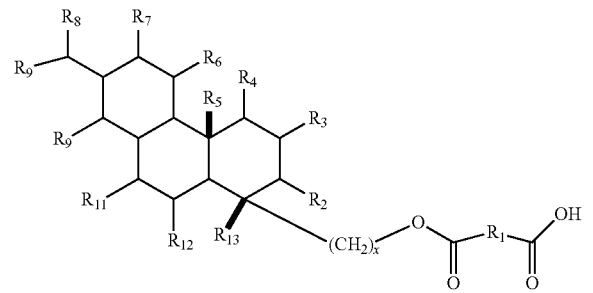

where $R_1$ of Formula II is:
a) an alkylene group, including substituted and unsubstituted alkylene groups, wherein hetero atoms selected from the group consisting of oxygen, nitrogen, silicon, phosphorus, fluorine, chorine, bromine and iodide, either may or may not be present in the alkylene group;
b) an arylene group, including substituted and unsubstituted arylene groups, wherein hetero atoms either may or may not be present in the arylene group;
c) an arylalkylene group, including substituted and unsubstituted arylalkylene groups, wherein hetero atoms either may or may not be present in either or both of the alkyl portion and the aryl portion of the arylalkylene group; or
d) an alkylarylene group, including substituted and unsubstituted alkylarylene groups, wherein hetero atoms either may or may not be present in either or both of the alkyl portion and the aryl portion of the alkylarylene group;
two or more substituents can be joined together to form a ring; and
each of $R_2$-$R_{13}$ are independently selected from the group consisting of hydrogen, alkyl groups, arylalkyl groups, alkylaryl groups, and heterocyclic groups; and wherein x is an integer of one or more.

17. The composition of claim 16, wherein $R_1$ of Formula II is an alkylene group having the structure —$(CH_2)p$- in which p is an integer in a range of from about 2 to about 12.

18. The composition of claim 16, wherein the amount of at least one ester compound represented by General Formula I is in the range of from about 50% to about 95% by weight of the composition.

19. The composition of claim 16, wherein the amount of at least one ester compound represented by General Formula II is in the range of from about 5% to about 50% by weight of the composition.

20. The composition of claim 16, wherein x of Formula II is an integer from 1 to 20.

* * * * *